(12) United States Patent
Ang

(10) Patent No.: US 6,291,436 B1
(45) Date of Patent: *Sep. 18, 2001

(54) DIRECT ACTION ANTI-MYCOTIC

(75) Inventor: Jit F. Ang, Chesterfield, MO (US)

(73) Assignee: International Fiber Corporation, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/354,829

(22) Filed: Jul. 16, 1999

(51) Int. Cl.$^7$ ........................................ A61K 31/70
(52) U.S. Cl. ................................ 514/31; 536/6.5
(58) Field of Search ................ 514/31; 536/6.5

(56) References Cited

U.S. PATENT DOCUMENTS 4,536,494 * 8/1985 Carter ..................................... 514/31
5,776,904 * 7/1998 Seki et al. ............................. 514/31

* cited by examiner

*Primary Examiner*—Elli Peselev
(74) *Attorney, Agent, or Firm*—Hodgson Russ LLP

(57) ABSTRACT

A direct action anti-mycotic composition is provided which is a natamycin material having an average particle diameter of 10 microns or less and/or an average surface area to weight ratio of at least 2 m$^2$/g. The natamycin material may be utilized in a form fit for human consumption on or in perishable material susceptible to spoilage by mold, yeast, or flingal growth. The natamycin material provides effective protection to a perishable material from mold, yeast, or fungal growth at concentrations of from 1 ppm to 5 ppm and higher. Methods are also provided for formulating and utilizing the natamycin material.

21 Claims, 2 Drawing Sheets

DIRECT ACTION ANTI-MYCOTIC

FIELD OF THE INVENTION

The present invention relates to a novel direct action anti-mycotic composition, compositions containing the novel direct action anti-mycotic material, and methods of using the compositions.

BACKGROUND OF THE INVENTION

Certain foods are perishable materials which are susceptible to mold, yeast, or fungal growth. Mold, yeast, or fungal growth in such foods can drastically reduce the usable life span of the foods. For example, dairy products, particularly cheese, and meat products, particularly fermented meat products such as sausages and pepperoni, are especially susceptible to being rendered unfit to eat by the growth of molds, yeast, and fungi.

Anti-mycotic materials are materials which inhibit mold, yeast, and fungal growth. Anti-mycotic materials are commonly added to perishable foods susceptible to mold, yeast, or fungal growth to inhibit the growth of such materials in the food and extend the shelf-life of the foods.

Anti-mycotic materials which are added to foods to extend the usable life span of the foods act by either an indirect or a direct mechanism to inhibit the growth of molds, yeasts and fungi. Indirect action anti-mycotics are materials such as enzyme/carbohydrate mixtures which react in combination with oxygen in a sealed package of food to scavenge and deplete oxygen in the package containing the anti-mycotic mixture, thereby inhibiting the growth of oxygen dependent molds, yeast, and fungi. Direct action anti-mycotics are materials applied in or on a food which inhibit the growth of a mold, yeast, or fungus upon direct contact with the mold, yeast, or fungus, often by inhibiting the development of mold, yeast, or fungus cell membranes. Direct action anti-mycotic materials are often preferable to indirect action anti-mycotics since indirect action anti-mycotics are only effective while a food material remains sealed in a package, and do not provide continuing anti-mycotic protection after the package of food is opened.

A particularly preferred direct action anti-mycotic is natamycin. Natamycin is one the few direct action anti-mycotics which is approved as a food additive by the Food and Drug Agency of the U.S. government. Natamycin is commercially available, for example as Delvocide® from Gist-Brocades Food Ingredients, Inc., King of Prussia, Pa. 19406, or as Natanaxe® from Cultor Food Science (address). Commercially available natamycin may be obtained in a pure form, or may be cut with a diluent such as lactose or sodium chloride.

Natamycin materials are active at relatively low concentrations. In an agar medium natamycin has been shown to have anti-mycotic activity at concentrations upwards from 1 part per million ("ppm"). In an animal feed mixture, U.S. Pat. No. 5,902,579 discloses that 1.1–110 ppm of the anti-mycotic natamycin can be provided in the feed mixture in a fermentation biomass.

Prior to the present invention, however, concentrations of greater than 5 ppm of natamycin have been necessary for effective mold, yeast, and fungus control in non-liquid foods for human consumption, in part since conventional natamycin which is fit for human consumption does not have sufficient anti-mycotic activity to prevent mold, yeast, or fungal growth when spread uniformly at very low concentrations in the food material. In the dairy industry, for example, concentrations of greater than 5 ppm, typically from 6 ppm to 20 ppm, of natamycin are required to provide effective protection of a dairy food such as cheese from spoilage due to mold, yeast, or fungus growth.

It is desirable to provide a natamycin material which has effective anti-mycotic activity at very low concentrations. Natamycin is an extremely expensive commodity, and reduction of the amount required for effective anti-mycotic activity in a food fit for human consumption offers significant cost advantages.

SUMMARY OF THE INVENTION

In one aspect, the present invention is an anti-mycotic material comprising a particulate natamycin material having an average particle diameter of 10 microns or less. In a preferred embodiment, the composition further includes a particulate anti-caking material in contact with particles of natamycin. In another aspect, the present invention is an anti-mycotic composition containing a natamycin material which has an average surface area to weight ratio of at least 2 $m^2/g$. In a preferred embodiment, the composition further includes a particulate anti-caking material in contact with particles of natamycin.

In yet another aspect, the present. invention is a composition comprising a perishable food material and a natamycin material fit for human consumption which is dispersed in or on the perishable food material. The perishable food material is susceptible to spoilage from mold, fungus, or yeast growth. The natamycin material is present in the food material in concentrations of from 1 part per million up to 5 parts per million and provides effective anti-mycotic activity to the food material. The present invention also encompasses a method of providing a perishable food material protection from yeast, mold, or fungus growth by dispersing a natamycin material in the food material so that natamycin is present in the food material in concentrations of 1 ppm up to 5 ppm. The anti-mycotic material is effective to provide protection against mold, fungus, or yeast growth at natamycin concentrations of 1 to 5 ppm.

In another aspect, the present invention is a composition comprising a perishable material susceptible to spoilage from mold, fungus, or yeast growth and a natamycin material dispersed in or on the perishable material, where the natamycin material has an average particle diameter of 10 microns or less. The invention also encompasses a method of providing a perishable material protection from fungus, yeast, and mold growth in which a natamycin material having an average particle diameter of 10 microns or less is dispersed in the perishable material, In still another aspect, the invention is a composition comprising a perishable material susceptible to spoilage from mold, yeast, or fungus growth and a natamycin material having surface to weight ratio of at least 2 $m^2/g$ dispersed in the perishable material. The invention also encompasses a method of providing a perishable material protection from yeast, fungus, and mold growth in which a natamycin material having a surface area to weight ratio of at least 2 $m^2/g$ is dispersed in the perishable material.

DESCRIPTION OF THE PREFERRED EMBODIMENTS

As used herein the term "effective", when used to describe anti-mycotic activity, is defined to mean: able to prevent visible growth of molds, yeasts, and fungi on or in a medium susceptible to such growth at a temperature of 40° C.–45° C. for a period of at least 40 days. The phrase "fit for human consumption" is defined to mean a food or ingredient which is recognized as safe for human ingestion. The term "anti-caking material", as used herein, is defined as a material which enhances the flow characteristics of a substrate into which the anti-caking material is dispersed. The term "diluent" is used in accordance with its conventional meaning, but specifically includes diluents which are solids such as powdered lactose or sodium chloride. The term "natamycin material", as used herein, means natamycin plus any diluents that have been mixed with the natamycm.

Figure 1:
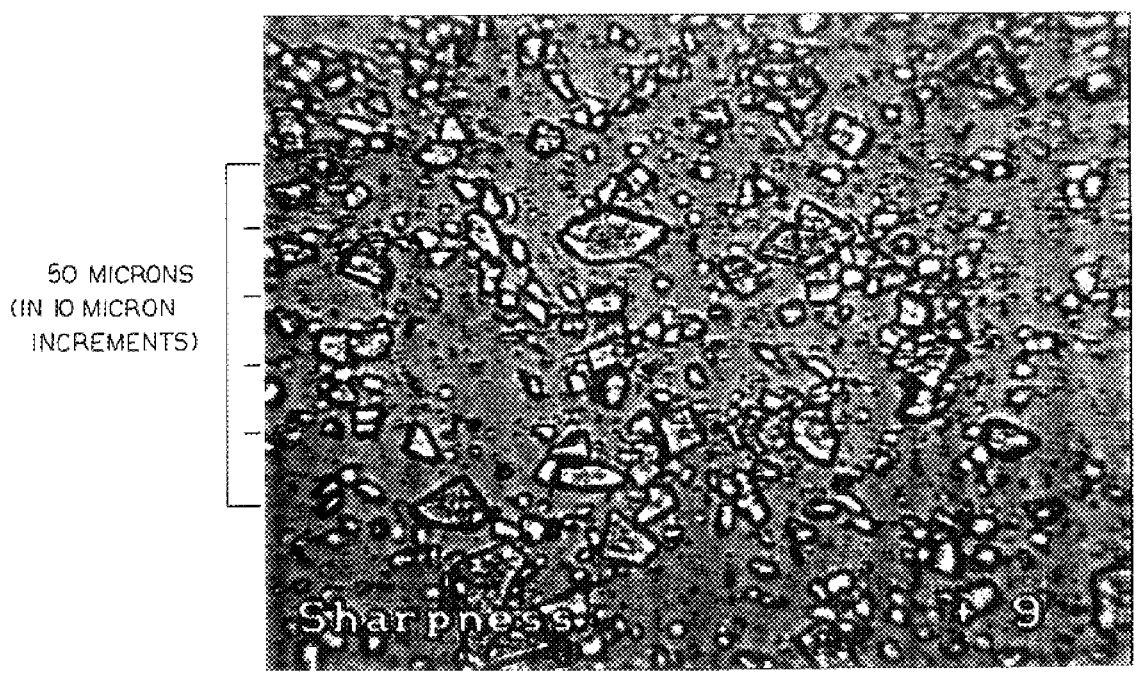
FIG. 1 is a photograph of a conventional commercially available natamycin material at 800x magnification.

Conventional, commercially available natamycin compositions contain many large irregularly shaped particles, as shown in FIG. 1. Typically the average particle size of such conventional natamycin compositions ranges from between 10 microns and 60 microns in diameter. Smaller particle sizes are avoided since excessive processing measures are required to produce a natamycin material with an average particle diameter of 10 microns or less, and because such small particles (10 microns or less in diameter) tend to agglomerate to form larger particles when the particles are maintained in a dry state.

The present invention resides in the discovery that a particulate natamycin material of very small particle diameter, specifically 10 microns or less in average diameter, is signficantly more effective as an anti-mycotic than a larger particle diameter conventional natamycin material. The natamycin material of the present invention has a large surface area to weight ratio relative to conventional natamycin materials due to its small particle size. Therefore, the natamycin material of the present invention is more effective to inhibit the growth of molds, yeast, and fingi than conventional natamycin materials since more surface area of the natamycin material is available for direct contact with any mold, yeast, or fungus per unit weight of the natamycin material.

Furthermore, the small particle size of the present natamycin material permits the anti-mycotic to be dispersed more uniformly per unit weight on or in a substrate, thereby providing more effective protection of the entire substrate from mold, yeast, and fungus growth. As a result of relative particle size, conventional larger particle diameter natamycin compositions can leave patches of a substrate unprotected at low concentrations since it is more difficult to obtain uniform distribution of the larger particles at such low concentrations.

Figure 2:
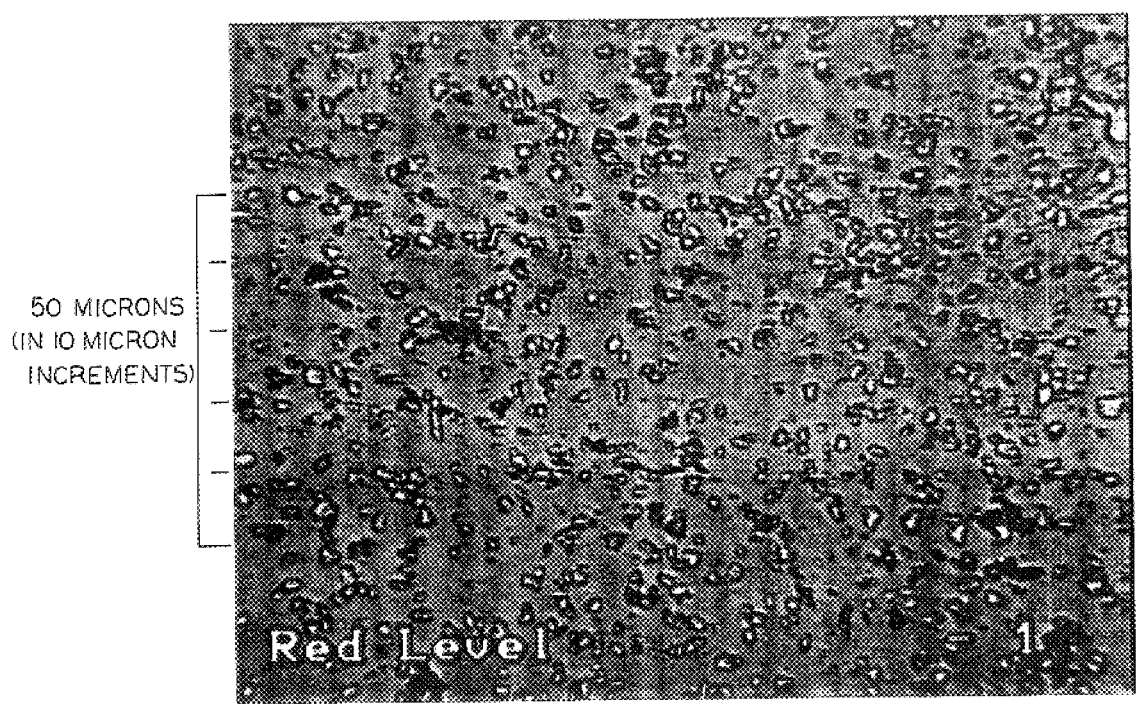
FIG. 2 is a photograph of a natamycin material of the present invention at 800x magnification.

The present invention, therefore, is a composition of a particulate natamycin material which has an average natamycin particle diameter of 10 microns or less, as shown in FIG. 2. Preferably the natamycin material has an average natamycin particle diameter of 7 microns or less, more preferably 5 microns or less, and most preferably 1 micron or less. The natamycin material may contain pure natamycin, or may contain La natamycin and at least one diluent such as lactose or sodium chloride, where the natamycin and the diluent are homogenously blended together. The natamycin material, therefore, may contain from 1% to 100% natamycin, by weight, and from 0% to 99% of a diluent, by weight. Preferably the natamycin material contains 50% or greater natamycin, by weight.

The present invention also includes a composition of a particulate natamycin material which has a natamycin surface area to weight ratio of at least two meters squared per gram ($2m^2/g$). More preferably the natamycin material has a natamycin surface area to weight ratio of at least 3 $m^2/g$. Again, the natamycin material may contain pure natamycin or may contain homogenously blended natamycin and at least one diluent such as lactose or sodium chloride in the relative weight percentages set forth above In a particularly preferred embodiment, the natamycin material has both an average natamycin particle diameter of 10 microns or less and a natamycin surface area to weight ratio of at least two meters squared per gram. Most preferably, the natamycin material has an average natamycin particle diameter of 1 micron or less and a natamycin surface area to weight ratio of at least 3 $m^2/g$.

A particulate natamycin material having an average particle diameter of less than 10 microns, or smaller, and/or a surface area to weight ratio of at least 2 $m^2/g$, or greater, in accordance with a composition of the present invention, may be formed from a natamycin starting material having an average particle diameter of greater than 10 microns and surface to weight ratio of less than 2 $m^2/g$. Such a natamycin starting material may be produced by a fermentation process utilizing *Streptomyces natalensis* or *S. chattanoogenisis*. Fermentation methods for producing natamycin have been known for years. A conventional fermentation process for producing natamycin which may be used as the natamycin starting material is disclosed in British Patent No. 846,933 (1960), which is hereby incorporated by reference. More preferably, the natamycin starting material is a commercially available natamycin composition such as Delvocide® or Natamax®. A commercially available natamycin starting material may contain diluents such as lactose or sodium chloride, and, if desired, such diluents may be added to a natamycin starting material produced by a fermentation process in a desired amount.

In one embodiment of the present invention, the natamycin starting material is milled or ground to (i) reduce the physical dimensions of the particles of natamycin in the natamycin starting material to an average particle diameter of 10 microns or less, more preferably 7 microns or less, even more preferably 5 microns or less, and most preferably 1 micron or less; and/or (ii) to alter the physical dimensions of the particles of natamycin so that the natamycin in the natamycin material has a surface area to weight ratio of at least 2 $m^2/g$, and more preferably at least 3 $m^2/g$. If the natamycin starting material contains a diluent, the diluent may also be reduced in physical particle size or increased in surface area to weight ratio by the milling or grinding process, however, the diluent is not to be included in the average particle diameter and/or surface area to weight measurements of the natamycin in the natamycin material. Typically, the analytical measurements of the average particle diameter and surface area to weight are conducted in solutions in which the diluent is soluble and natamycin is not, so the diluent has no effect on the measurements.

The natamycin starting material may by milled or ground using conventional milling and grinding equipment and processes used for fine grinding. Processing methods for fine grinding which may be used to form the natamycin material of the invention include air jet milling, plate grinding, media grinding, hammer milling, homogenizing, and colloid milling. Ground particles of the natamycin material which have been ground to an acceptable size are separated from larger particles, preferably by screening, filtering, or air classifying, and collected to provide the natamycin material.

Air jet milling is a particularly preferred method of fine grinding the natamycin starting material into the natamycin material of the invention. The natamycin starting material is charged into a hopper which conveys the natamycin starting material into a grinding chamber via a screw feeder. In the grinding chamber the material is ground by airflows from the nozzles at the base of the mill, which cause the particles to collide and grind against themselves. Particles that reach a selected size in accordance with the dimensions of the natamycin particles of the invention are passed through a separator and conveyed to a collector. Particles that are too large are returned to the grinding chamber for additional processing.

In another embodiment of the present invention, the natamycin starting material is sifted to separate a natamycin material having (i) an average natamycin particle diameter of 10 microns or less, more preferably 7 microns or less, even more preferably 5 microns or less, and most preferably 1 micron or less; and/or (ii) having a natamycin surface area to weight ratio of at least 2 $m^2/g$, and more preferably at least 3 $m^2/g$. Conventional sifting and classifying equipment and processes may be utilized to separate the fine natamycin particles from larger particles, where screening and air classifying processes are particularly preferred. The maximum particle diameter of the separated natamycin material may be selected by choosing the appropriate separation equipment.

The natamycin material recovered from the grinding and/or sifting process may be used, as is, as a dry. particulate anti-mycotic, or may be further processed as a dry preparation or as a wet preparation to enhance or maintain the efficacy of the natamycin material. The natamycin material may be further processed as a dry preparation by combining the natamycin material with an anti-caking material. The anti-caking material can be combined with the fine particulate natamycin material to inhibit and prevent the fine particles from reagglomerating into larger particles which are detrimental to the anti-mycotic efficacy of the natamycin material.

The anti-caking material utilized is a food-grade material which is effective for reducing agglomeration of the natamycin material. The anti-caking material should be able to absorb and retain moisture. Anti-caking materials which may be utilized in conjunction with the natamycin material include food grade celluloses, including powdered cellulose and microcrystalline cellulose, silicates, phosphates, starches, clays, including bentonite and montmorillite clays, minerals, flours, including rice flour, wheat flour, corn flour, and soy flour, polysaccharides, fibers, and combinations thereof.

The anti-caking material can be combined with the natamycin material at levels of from 0.001 to 99.999% of anti-caking material, by weight of the combined anti-caking material and the natamycin material. More preferably, the anti-caking material is present in combination with the natamycin material at levels of from 0.1 to 20% anti-caking material, by weight, and most preferably is present at levels of from 1 to 10%, by weight.

In one embodiment of the invention, the anti-caking material may be utilized as a functional food ingredient to inhibit caking and enhance the flowability of a divided food material in which the anti-caking material is dispersed, and the natamycin material is blended with the anti-caking material to provide anti-mycotic activity for the divided food material. A divided food material in which the anti-caking/ natamycin material may be dispersed, for example, is a shredded or grated cheese. When the anti-caking material is to be used as a functional food ingredient to enhance flowability in a food material, the anti-caking material should be present in greater quantity in the anti-caking/ natamycin blend than when the anti-caking material is utilized solely for the purpose of preventing agglomeration of the natamycin material. Preferably, when the anti-caking material is to be used as a functional food ingredient, the anti-caking material is present in from about 90%–99.99%, by weight, of the combined anti-caking material and the natamnycin material.

The anti-caking material and natamycin material can be combined by conventional means and with conventional equipment for mixing dry particulate materials. The anti-caking material and the natamycin material are preferably mixed to form a homogenous blend to ensure contact between particles of the natamycin material and the anti-caking material, enhancing the anti-agglomeration effects of the anti-caking material on the natamycin material. In a particularly preferred embodiment, the anti-caking material and the natamycin material are mixed to a homogenous blend in a ribbon-type blender. In a most preferred embodiment, the natamycin material is suspended in a liquid such as lecithin or water, and the suspension is sprayed onto the anti-caking material, preferably by a conventional spray drying apparatus, while the anti-caking material is being agitated to uniformly coat the anti-caking material with the suspension of natamycin material.

The natamycin material may also be ftrther processed as a wet preparation by dispersing the natamycin material in a liquid, where the wet preparation of the natamycin material may be applied to a perishable material susceptible to mold, yeast, and fungal growth to provide the perishable material the anti-mycotic activity of the natamycin material in the wet preparation. The liquid inhibits the fine particles of the natamycin material from agglomerating to form larger particles by forming a liquid barrier around the particles which prevents the particles from interacting and reassociating into larger particles. The liquid in which the natamycin material may be dispersed to form the wet preparation of natamycin may be any food grade liquid, regardless of the solubility of the natamycin in the liquid. Preferred liquids used to form the wet preparation of natamycin are edible oils, water, food grade alcohols, carbohydrate solutions, hydrocolloid solutions, polyols, and fats. Especially preferred oils include canola oil, annato oil(soluble), soy oil, peanut oil, corn oil, cottonseed oil, sunflower seed oil, and lecithin. The most preferred liquids for forming a wet preparation of the natamycin material are water and lecithin.

A wet preparation of the natamycin material may be formed by combining the natamycin material and a selected liquid. Preferably the amount of natarnycin material uitlized in the wet preparation is from 0.0001% to 20%, weight of natamycin material per volume of liquid ("w/v"), and more preferably from 0.001% to 10%, w/v. If the natamycin material is insoluble in the liquid, the liquid and natamycin material are mixed to disperse and suspend the natamycin material in the liquid prior to application of the wet preparation to a perishable material requiring anti-mycotic protection so the natamycin material may be uniformly dispersed on or into the perishable material. The liquid and natamycin material may be mixed by conventional means for agitating, mixing, and dispersing a solid material in a liquid such as a blender.

Further ingredients may be added to the natamycin material, either as a wet preparation or a dry preparation, to provide desirable characteristics to a material in which the natamycin material is utilized. Salts, phosphates, and silicates may be combined with the natamycin material to provide anti-agglomeration properties to the mixture. Surface tension agents such as sodium laural sulfate (dodecyl) may also be combined with the natamycin material. Coloring agents, for example annato oil and paprika, can be used to provide color to the natamycin material. Flavors, seasonings, and spices can be added to the natamycin material to deliver improved food functionality to the natamycin material. Enzymes can be added to the natamycin material to enhance the flavor of fermented or ripened food materials in which the natamycin material is utilized.

The natamycin material, either as a dry preparation or a wet preparation, and with or without further added ingredients, may be utilized with a perishable material susceptible to spoilage from mold, fungus, or yeast to protect the perishable material from such spoilage. The natamycin material has the characteristics described above, either having an average particle diameter of 10 microns or less(preferably 5 or 1 micron or less), a surface area to weight ratio of at least 2 $m^2/g$ (preferably at least 3 $m^2/g$), or both. The perishable material may be any material which is susceptible to spoilage or damage from mold, yeast, or fungal growth, but preferably is a food material. More preferably, the natamycin material is utilized with a non-liquid food material susceptible to mold, yeast, and fungal growth, and preferably the non-liquid food material is a cheese or a fermented meat, including sausage and pepperoni meats. Most preferably the natamycin material is fit for human consumption and is dispersed on or in a perishable food material so that natamycin is present in the composition of the food material and natamycin material in a concentration of from 1 part per million to 5 parts per million, where the natamycin provides effective anti-mycotic activity for the perishable food material at such concentrations.

The natamycin material is dispersed on or in the perishable material, depending on the nature of the perishable material. For example, the natamycin material may be dispersed in a grated or shredded cheese material and may be dispersed on a sausage link or a solid block of cheese.

The natamycin material may be dispersed on or in the perishable material in several ways, depending on the nature of the perishable material in or on which the natamycin material is to be dispersed, and on the nature of the natamycin material as a wet or dry preparation. A wet preparation of the natamycin material may be applied to the perishable material by dipping the perishable material into the wet preparation of the natamycin material, or by spraying the wet preparation of the natamycin material onto the perishable material. If the natamycin material is insoluble in the liquid used in the wet preparation, the natamycin material should be agitated in the liquid prior to application of the wet preparation to the perishable material to suspend the natamycin material in the liquid for uniform distribution of the natamycin material to the perishable material.

A dry preparation of the natamycin material (or the dry particulate natamycin material itself) may be dispersed in or on the perishable material by dusting the natamycin material on the perishable material or by blending the natamycin material and the perishable material into a homogenous blend. The dry preparation of the natamycin material may be blended together with the perishable material using conventional processes and equipment for dry blending materials, for example a ribbon blender. If the natamycin material is mixed with an anti-caking material, the dry preparation of the natamycin material and anti-caking material is preferably added to the perishable material so that the natamycin material is blended into the perishable material while maintaining contact with the anti-caking material to prevent reagglomeration of the natamycin material upon dispersion into the perishable material.

In a particularly preferred embodiment, a liquid suspension is formed of the natamycin material, the liquid suspension of the natamycin material is sprayed onto an anticaking material, and the anti-caking material coated with the natamycin material is added to a perishable food material, preferably a grated or shredded cheese, as a functional food ingredient which prevents caking of the food material and provides anti-mycotic activity. The liquid suspension of the natamycin material is formed by mixing the natamycin material and a liquid, preferably water or lecithin, while agitating the mixture. The liquid suspension is preferably sprayed on the anti-caking material with a conventional spray dryer while agitating the anti-caking material. The anti-caking material is mixed with the perishable food material by dry blending the anti-caking material and the food material.

The following examples provide non-limiting embodiments of the present invention.

EXAMPLE 1

Commercial natamycin, diluted to about 50% with lactose, is obtained from two separate suppliers. A control sample is retained from each of the commercial natamycin materials, and a sample of each of the commercial natamycin materials is individually ground by processing the sample through an air jet mill to form a natamycin material in accordance with the present invention. The average particle sizes of each of the natamycin samples are analyzed with a Coulter Particle Size Analyzer. The results of the size analysis is shown in Table 1.

TABLE 1

| Sample | Mean Diameter ($\mu$m) | Median Diameter ($\mu$m) |
|---|---|---|
| Commercial Sample 1 | 29.23 | 14.83 |
| Refined Sample 1 | 2.65 | 2.56 |
| Commercial Sample 2 | 16.43 | 12.61 |
| Refined Sample 2 | 2.54 | 2.58 |

As shown in Table 1, the commercially available natamycin material has an average diameter substantially greater than 10 microns, and the natamycin material produced by grinding a commercial natamycin material in an air jet mill has an average diameter less than 10 microns.

EXAMPLE 2

Commercial natamycin, diluted to about 50% with lactose, is obtained from two separate suppliers. A control sample is retained from each of the commercial natamycin materials, and a sample of each of the commercial natamycin materials is individually ground by processing the sample through an air classifying mill to form a natamycin material in accordance with the present invention. The average particle sizes of each of the natamycin samples are analyzed with a Coulter Particle Size Analyzer. The results of the size analysis is shown in Table 2.

TABLE 2

| Sample | Mean Diameter ($\mu$m) | Median Diameter ($\mu$m) |
|---|---|---|
| Commercial Sample 1 | 29.23 | 14.83 |
| Refined Sample 1 | 8.15 | 8.02 |

TABLE 2-continued

| Sample | Mean Diameter (μm) | Median Diameter (μm) |
|---|---|---|
| Commercial Sample 2 | 16.43 | 12.61 |
| Refined Sample 2 | 8.24 | 8.02 |

As shown in Table 2, the commercially available natamycin material has an average diameter substantially greater than 10 microns, and the natamycin material produced by grinding a commercial natamycin material in an air classifying mill has an average diameter less than 10 microns.

EXAMPLE 3

Commercial natamycin, diluted to about 50% with lactose, is obtained from two separate suppliers, and these are combined in a 1:1 ratio based on weight. A pure sample of the mixture of the commercial natarnycin is retained, and another sample of the commercial natamycin is treated with 5% by weight of tricalcium phosphate (an anti-agglomerating agent). A sample of the pure combined commerical natamycin material and a sample of the combined commercial natamycin material with tricalcium phosphate are refined in an air jet mill. The particle size of the samples and the specific surface area of the natamycin samples are analyzed with a Malvern Mastersizer. The results are shown in Table 3.

TABLE 3

| Sample | Mean Diameter (μm) | Specific Surface Area (m²/g) |
|---|---|---|
| Commercial Blend | 57.2 | 0.86 |
| Refined Blend | 5.04 | 3.4 |
| Comm. Blend w/Ca$_3$(PO$_4$)$_2$ | 54.02 | 0.99 |
| Refined Blend w/Ca$_3$(PO$_4$)$_2$ | 4.78 | 3.44 |

As shown by the data in Table 3, the mean particle size of the refined particles is reduced to less than 10 microns and the surface area per unit weight of the refined natamycin material is greater than 2 m$^2$/g. In contrast, the commercial natamycin material, whether blended with an anti-agglomerating agent or not, has an average particle diameter substantially greater than 10 microns, and a specific surface area per unit weight which is less than 1 m$^2$/g.

EXAMPLE 4

The efficacy of a refined natamycin material prepared in accordance with the present invention in preventing yeast, mold, or fungal spoilage is compared to that of a conventional natamycin material and a control having no antimycotic material on an anti-caking material in cheese samples. Three combination anti-caking material/natamycin material samples are prepared containing the following levels of ingredients, by weight:

Sample 1: 0.05% (2.5 ppm) conventional natamycin material (commercial sample 2 from Example 1 above); 96.43% powdered cellulose (anti-caking material); 1% lecithin; and 2.52% water; Sample 2: 0.05% (2.5 ppm) refined natamycin material (refined sample 2 from Example 2 above; 96.43% powdered cellulose (anti-caking material); 1% lecithin; and 2.52% water; and Sample 3: 0.18% (9 ppm) conventional natamycin material (commercial sample 2 from Example 1 above); 96.24% cellulose (anti-caking material); 1% lecithin; and 2.58% water.

The combined anti-caking material/natamycin material samples are each prepared by loading the cellulose into a ribbon-type blender and blending for a few minutes. The lecithin is heated to reduce its viscosity and the required amount of lecithin is atomized into the cellulose in the blender with the blender running. Separately, the required amount of natamycin material is suspended in the water. The natamycin material suspension is then atomized into the cellulose/lecithin in the blender with the blender running. After all the natamycin material suspension is added, blending is continued for an additional amount of time to ensure a homogenous blend.

The efficacy of the anti-caking/natamycin material samples is then tested in shredded mozzarella cheese. Each sample is added to a separate cheese sample in an amount of 1% of the anti-caking/natamycin material, by weight, to 99% of the cheese, by weight. A control sample of cheese containing no anti-caking agent and no natamycin material is also prepared (Sample 4), as well as a control sample of cheese containing 1% pure cellulose anti-caking material by weight (Sample 5). Ten bags of each cheese sample are prepared and are stored in a cold room at 40° F. for the duration of the test. The 10 bags of each sample are visually examined for growth of yeast/mold/ or fungus at 46, 74, 106, 145, 179, 193, and 223 days. The ratio of bags having visible growth of mold/yeast/or fungus growth is recorded. The results are shown in Table 4.

TABLE 4

Number of Spoiled Bags (x/10)

| Days Stored | Sample 1 Conv. 2.5 ppm | Sample 2 Refined 2.5 ppm | Sample 3 Conv. 9 ppm | Sample 4 Control No add. | Sample 5 Control Cellulose |
|---|---|---|---|---|---|
| Day 46 | 1/10 | 0/10 | 0/10 | 7/10 | 9/10 |
| Day 74 | 5/10 | 0/10 | 0/10 | 9/10 | all |
| Day 106 | 9/10 | 3/10 | 0/10 | all | all |
| Day 145 | all | 4/10 | 3/10 | all | all |
| Day 179 | all | 5/10 | 4/10 | all | all |
| Day 193 | all | 6/10 | 5/10 | all | all |
| Day 223 | all | 9/10 | 8/10 | all | all |

As shown by the data in Table 4, the refined natamycin material of the present invention is more efficacious than a conventional natamycin material at concentrations of less than 5 ppm, and the refmed natamycin material at a concentration of 2.5 ppm is about as effective at preventing mold, yeast, and fungal growth in cheese as conventional natamycin at 9 ppm. Both the conventional and the refined natamycin materials are more effective at preventing mold, yeast, and fungal growth than pure cellulose.

Those who are skilled in the art will readily perceive how to modify the invention. Therefore, the appended claims are to be construed to cover all equivalent structures, compositions, and processes which fall within the true scope and spirit of the invention

What is claimed is:

1. A composition, comprising:
a perishable solid food material which is susceptible to spoilage from mold, fungus, or yeast growth in the material;
a natamycin material fit for human consumption having an average particle diameter of 9 microns or less dispersed in or on said perishable food material, said natamycin material providing effective anti-mycotic activity for said perishable food material at concentrations of from 1 part per million up to 5 parts per million of natamycin.

2. The composition of claim 1 wherein said natamycin material is a particulate material having a surface area to weight ratio of at least 2 m$^2$/g.

3. The composition of claim 1 wherein said perishable food material is a cheese.

4. The composition of claim 1 further comprising an anti-caking material dispersed in said perishable food material, wherein said natamycin material is in contact with said anti-caking material.

5. The composition of claim 4 wherein said anti-caking material is selected from the group consisting of powdered cellulose, microcrystalline cellulose, silicates, clays, flours, starches, fibers, polysaccharides, and combinations thereof.

6. A method for providing a perishable solid food material which is susceptible to yeast, fungus, or mold growth protection from yeast, fungus, or mold growth, comprising dispersing a natamycin material fit for human consumption having an average particle diameter of 9 microns or less in or on said perishable food material so that natamycin is present contacting said perishable food material, said natamycin material being sufficient to provide effective anti-mycotic activity for said perishable food material.

7. The method of claim 6 wherein said natamycin material having an average particle diameter of 9 microns or less is obtained by grinding a natamycin material having an average diameter of greater than or equal to 9 microns and/or separating a ground natamycin material having an average particle diameter of less than 9 microns.

8. The method of claim 6 wherein said natamycin materialthas a surface area to weight ratio of at least 2 m$^2$/g.

9. The method of claim 8 wherein said natamycin material having a surface area to weight ratio of at least 2 m$^2$/g is obtained by grinding a natamycin material having a surface area to weight ratio of less than 2 m$^2$/g and/or separating a ground natamycin material having a surface area to weight ratio of at least 2 m$^2$/g.

10. The method of claim 6 wherein said food material is a cheese.

11. The method of claim 10 wherein said natamycin material is dispersed in said cheese along with an anti-caking material, said natamycin material being located in contact with said anti-caking material.

12. The method of claim 6 wherein said natamycin material is dispersed in said perishable food material along with an anti-caking material, said natamycin material being located in contact with said anti-caking material.

13. The method of claim 6 wherein said natamycin material is dispersed on said perishable food material by dipping said perishable food material in an liquid suspension of said natamycin material.

14. The method of claim 6 wherein said natamycin material is a dry particulate material which is dispersed in said perishable food material by blending said natamycin material and said perishable food material.

15. The method of claim 6 wherein said natamycin material is dispersed on or in said perishable food material by spraying an liquid suspension of said natamycin material on or into said perishable food material.

16. A composition, comprising:
a perishable solid food material which is susceptible to spoilage from mold, fungus, or yeast growth in the material;
a natamycin material fit for human consumption having an average particle diameter of 7 microns or less dispersed in or on said perishable food material, said natamycin material providing effective anti-mycotic activity for said perishable food material at concentrations of from 1 part per million up to 5 parts per million of natamycin.

17. A composition, comprising:
a perishable solid food material which is susceptible to spoilage from mold, fungus, or yeast growth in the material;
a natamycin material fit for human consumption having an average particle diameter of 5 microns or less dispersed in or on said perishable food material, said natamycin material providing effective anti-mycotic activity for said perishable food material at concentrations of from 1 part per million up to 5 parts per million of natamycin.

18. A composition, comprising:
a perishable solid food material which is susceptible to spoilage from mold, fungus, or yeast growth in the material;
a natamycin material fit for human consumption having an average particle diameter of 1 micron or less dispersed in or on said perishable food material, said natamycin material providing effective anti-mycotic activity for said perishable food material at concentrations of from 1 part per million up to 5 parts per million of natamycin.

19. A method for providing a perishable solid food material which is susceptible to yeast, fungus, or mold growth protection from yeast, fungus, or mold growth, comprising dispersing a natamycin material fit for human consumption having an average particle diameter of 7 microns or less in or on said perishable food material in a concentration of from 1 part per million up to 5 parts per million, said concentration of natamycin being sufficient to provide effective anti-mycotic activity for said perishable food material.

20. A method for providing a perishable solid food material which is susceptible to yeast, fungus, or mold growth protection from yeast, fungus, or mold growth, comprising dispersing a natamycin material fit for human consumption having an average particle diameter of 5 microns or less in or on said perishable food material in a concentration of from 1 part per million up to 5 parts per million, said concentration of natamycin being sufficient to provide effective anti-mycotic activity for said perishable food material.

21. A method for providing a perishable solid food material which is susceptible to yeast, fungus, or mold growth protection from yeast, fungus, or mold growth, comprising dispersing a natamycin material fit for human consumption having an average particle diameter of 1 micron or less in or on said perishable food material in a concentration of from 1 part per million up to 5 parts per million, said concentration of natamycin being sufficient to provide effective anti-mycotic activity for said perishable food material.

* * * * *

UNITED STATES PATENT AND TRADEMARK OFFICE
CERTIFICATE OF CORRECTION

PATENT NO. : 6,291,436 B1
DATED : September 18, 2001
INVENTOR(S) : Jit F. Ang

It is certified that error appears in the above-identified patent and that said Letters Patent is hereby corrected as shown below:

<u>Column 11,</u>
Line 30, delete "t" and insert a space between "material" and "has"

Signed and Sealed this

Fourth Day of June, 2002

*Attest:*

*Attesting Officer*

JAMES E. ROGAN
*Director of the United States Patent and Trademark Office*